United States Patent
Yasuda et al.

(10) Patent No.: US 8,377,273 B2
(45) Date of Patent: Feb. 19, 2013

(54) GAS SENSOR

(75) Inventors: Toshikatsu Yasuda, Toki (JP); Haruhiko Shigeta, Iwakura (JP)

(73) Assignee: NGK Spark Plug Co., Ltd., Aichi (JP)

( * ) Notice: Subject to any disclaimer, the term of this patent is extended or adjusted under 35 U.S.C. 154(b) by 579 days.

(21) Appl. No.: 12/498,789

(22) Filed: Jul. 7, 2009

(65) Prior Publication Data
US 2010/0006433 A1 Jan. 14, 2010

(30) Foreign Application Priority Data

Jul. 9, 2008 (JP) ................................. 2008-178999
May 29, 2009 (JP) ................................. 2009-130245

(51) Int. Cl.
*G01N 27/407* (2006.01)
(52) U.S. Cl. .... 204/424; 73/23.31; 73/23.32; 205/784.5
(58) Field of Classification Search .......... 204/421–429; 73/19.01–31.07, 23.31, 23.32; 205/781, 205/783.5–785, 787
See application file for complete search history.

(56) References Cited

U.S. PATENT DOCUMENTS

| | | | | |
|---|---|---|---|---|
| 5,108,577 A | * | 4/1992 | Mase et al. | 204/426 |
| 5,215,643 A | * | 6/1993 | Kusanagi et al. | 204/412 |
| 6,562,215 B1 | * | 5/2003 | Nelson et al. | 204/421 |
| 6,580,280 B2 | * | 6/2003 | Nakae et al. | 324/717 |
| 6,770,180 B1 | | 8/2004 | Diehl | |
| 2003/0159928 A1 | | 8/2003 | Kojima et al. | |
| 2005/0189222 A1 | * | 9/2005 | Tsuzuki et al. | 204/424 |
| 2007/0017806 A1 | * | 1/2007 | Furuta et al. | 204/424 |

FOREIGN PATENT DOCUMENTS

| | | |
|---|---|---|
| JP | 63-208201 A | 8/1988 |
| JP | 9-326538 A | 12/1997 |
| JP | 2003-517605 A | 5/2003 |
| JP | 2003-322632 A | 11/2003 |

\* cited by examiner

*Primary Examiner* — J. Christopher Ball
*Assistant Examiner* — Jennifer Dieterle
(74) *Attorney, Agent, or Firm* — Sughrue Mion, PLLC

(57) ABSTRACT

A gas sensor includes a substantially cylindrical metal shell; a laminated sensor element held within the metal shell, and including a plate-shaped solid electrolyte layer extending in a longitudinal direction; an electrode portion provided on the solid electrolyte layer; an insulating layer; and a lead portion connected with the electrode portion, extending in the longitudinal direction, and having a front end portion laminated on the solid electrolyte layer, and a rear end portion laminated through the insulating layer on the solid electrolyte layer. The insulating layer has an end portion over and across which the lead portion extends, and which has a recessed shape, a raised shape, or a recessed and raised shape in the longitudinal direction as viewed in the lamination direction.

12 Claims, 6 Drawing Sheets

GAS SENSOR

BACKGROUND OF THE INVENTION

This invention relates to a gas sensor arranged to sense a concentration of a specified gas component in a measurement gas to be examined.

Conventionally, there is known a gas sensor using a laminated sensor element, as a gas sensor arranged to sense a concentration of a specified gas component in an exhaust gas discharged from an internal combustion engine of vehicle and so on, for a combustion control of the internal combustion engine. The laminated sensor element includes, for example, an element body, and a heater arranged to activate the element body by the heating.

U.S. Patent Application Publication No. 2003-159928 A1 (corresponding to Japanese Patent Application Publication No. 2003-322632) discloses a gas sensor including an element body having a cell and a heater. The cell has a solid electrolyte layer mainly made of, for example, zirconia, a pair of electrode portions mainly made of platinum and formed on both main surfaces of the solid electrolyte layer, and a pair of lead portions mainly made of platinum and connected with the pair of the electrode portions, and each of the pair of lead portions extending along the solid electrolyte layer. The heater has a pair of base layers mainly made of, for example, alumina, a heating portion mainly made of platinum and sandwiched between the pair of the base layers, and a pair of heater lead portions mainly made of platinum and connected with both end portions of the heating portion, and each of the pair of heater lead portions extending along an insulating layer.

SUMMARY OF THE INVENTION

Each of the lead portions is formed through the insulating layer on the solid electrolyte layer, except for a portion on the front end side which is connected with the electrode portion, for accurately sensing the concentration by suppressing catalytic reaction (catalysis). That is, the lead portion is formed to extend over and across (astride) an end portion of the insulating layer. However, the crack generates at the time of manufacture in a portion of the lead portion which extends over and across the end portion of the insulating layer. Consequently, output signal may not be picked up from the electrode portions.

In the sensor element, there are formed an unbaked solid electrolyte sheet 901 which becomes the solid electrolyte layer after the baking, as shown in FIG. 9A. An insulating paste is printed on the solid electrolyte sheet 901 to form an insulating pattern 902 which becomes the insulating layer after the baking. A conductive paste is screen-printed to form a lead pattern 905 which becomes the lead portion after the baking. Then, the entirety is dried, and baked to form the sensor element.

In this case, a surface of the insulating pattern 902 is one level higher relative to a surface of the solid electrolyte sheet 901. Therefore, the conductive paste is not sufficiently printed on an end portion 912 of the insulating pattern 902, especially on a corner portion of the end portion 912 of the insulating pattern 902. In this corner portion of the end portion 912 of the insulating pattern 902, the lead pattern becomes thin. The tensile stress is concentrated on the thin portion (astride portion m which extends over and across the insulating pattern 902) in response to constriction of the lead pattern 905 during the drying or the baking. Consequently, the crack generates.

It is, therefore, an object of the present invention to provide a gas sensor devised to solve the above mentioned problem, to suppress the generation of the crack in a lead portion which extends over and across an insulating layer, and to accurately sense a concentration.

According to one aspect of the present invention, a gas sensor comprises: a substantially cylindrical metal shell; a laminated sensor element held within the metal shell, the sensor element including: a plate-shaped solid electrolyte layer extending in a longitudinal direction; an electrode portion laminated on the solid electrolyte layer; and a lead portion connected with the electrode portion and extending in the longitudinal direction. The sensor element includes an insulating layer laminated on the solid electrode layer; and the lead portion has a front end portion directly laminated on the solid electrolyte layer, and a rear end portion laminated through the insulating layer on the solid electrolyte layer. The insulating layer has an end portion over and across which the lead portion extends, and which has a recessed shape, a raised shape, or a recessed and raised shape in the longitudinal direction as viewed in the lamination direction.

DETAILED DESCRIPTION OF THE INVENTION

Figure 1:
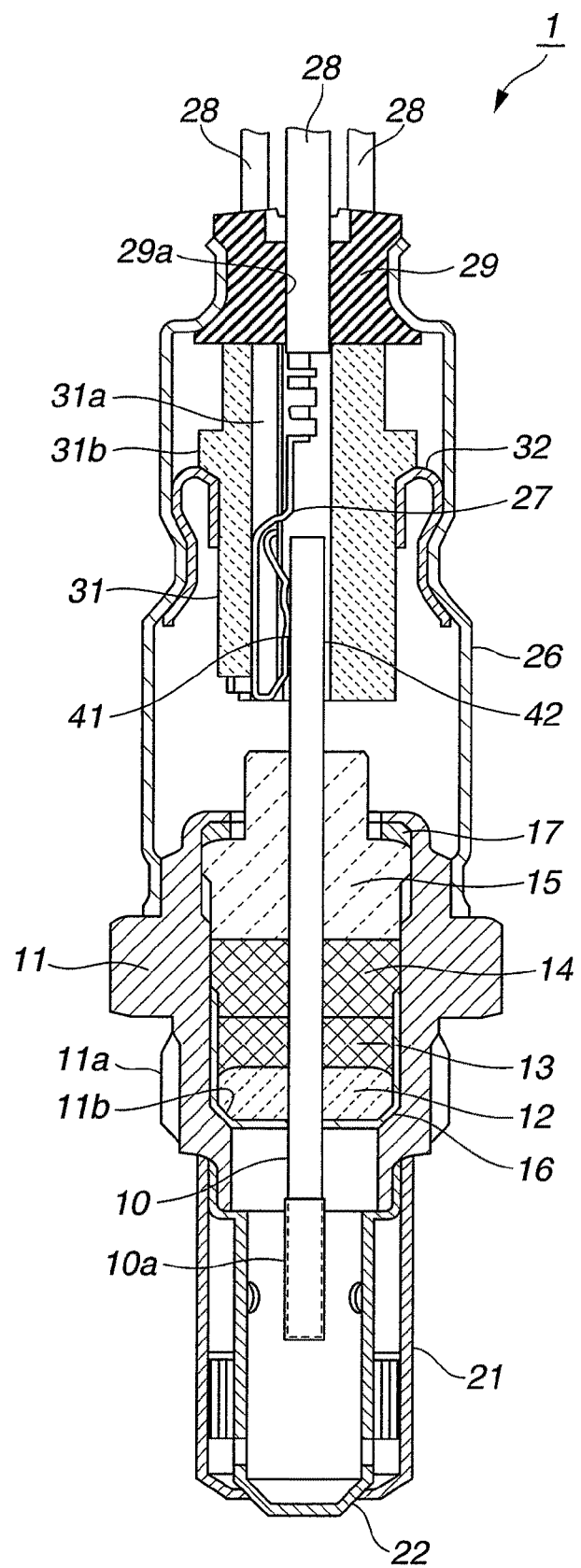
FIG. 1 is a sectional view showing a gas sensor according to a first embodiment of the present invention.

Hereinafter, gas sensors according to embodiments are illustrated below with reference to drawings. FIG. 1 is a sectional view showing a gas sensor according to a first embodiment of the present invention. The term "front" refers to a gas sensing side with respect to an axial direction of a gas sensor, and the term "rear" refers to a side opposite to the front side. This gas sensor 1 is a wide-range (or full-range) air-fuel ratio sensor which is for air-fuel ratio feedback control of internal combustion engines and vehicles, and which is mounted to exhaust pipes of these internal combustion engines and vehicles.

The gas sensor 1 includes a plate-shaped sensor element 10 which extends in the axial direction, and which is arranged to sense a specified gas in an exhaust gas which is a measurement gas to be examined; a cylindrical metal shell 11 which holds the sensor element 10 therein, and which is fixed to the exhaust pipe. The sensor element 10 is held to protrude from both end portions (a front end portion on a lower side of FIG. 1, and a rear end portion on an upper side of FIG. 1) of the metal shell 11. A porous front end protecting layer 10a is formed at a front end portion of the sensor element 10 which is a sensing portion, and which protrudes the front end portion of the metal shell 11.

The metal shell 11 includes a screw portion 11a located radially outside the metal shell 11, and arranged to fix the metal shell 11 to the exhaust pipe; and a shelf portion 11b which is located radially inside the metal shell 11, and which is a tapered surface having an inclination with respect to a plane perpendicular to the axial direction.

The gas sensor 1 includes an annular ceramic holder 12, powder-filled layers (hereinafter, referred to as talc rings 13 and 14), and a ceramic sleeve 15 which are disposed within the metal shell 11 in this order from the front end side (lower side in FIG. 1) to the rear end side (upper side in FIG. 1), and which surround an outer circumference portion of the sensor element 10. The gas sensor 1 includes a metal holder 16 disposed radially outside the ceramic holder 12 and the talc ring 13, and arranged to ensure the airtightness of the metal shell 11. Moreover, the gas sensor 1 includes a swage packing 17 disposed on a rear end portion of the ceramic sleeve 15. A rear end portion of the metal shell 11 is crimped so as to push the ceramic sleeve 15 through the crimping packing 17 toward the front end side.

The gas sensor 1 includes a pair of protectors (an outer protector 21 and an inner protector 22) which are mounted to the front end portion of the metal shell 11 by welding and so on, which are made of a metal such as stainless, which have a plurality of holes, and which surround the front end portion of the sensor element 10. Moreover, the gas sensor 1 includes an outer cylinder 26 which is fixed at the rear end portion of the metal shell 11, and which surrounds the sensor element 10. Moreover, the gas sensor 1 includes connection terminals 27; five lead wires (three wires shown in FIG. 1) 28 each having a front end portion electrically connected with one of the connection terminals 27, and a rear end portion electrically connected with external devices; a grommet 29 disposed on an opening portion of the outer cylinder 26 on the rear end side thereof (upper side in FIG. 1), and formed with lead wire holes 29a through which the lead wires 28 pass.

Within the outer cylinder 26, there are provided an insulating contact member 31 electrically connecting electrode terminal portions 41 and heater terminal portions 42 of the sensor element 10, and the connection terminals 27. The insulating contact member 31 has a cylindrical shape having a contact through hole 31a penetrating in the axial direction. The sensor element 10 and the connection terminals 27 are inserted into the contact through hole 31a of the insulating contact member 31. The connection terminals 27 are pressed to the electrode terminal portions 41 and the heater terminal portions 42 of the sensor element 10, so that the connection terminals 27 are electrically connected with the electrode terminal portions 41 and the heater terminal portions 42. These components form current paths between the electrode terminal portions 41 and the heater terminal portions 42 of the sensor element 10 and the external devices.

The insulating contact member 31 includes a collar portion or protruding portion 31b protruding from the insulating contact member 31 in the radially outward direction. The gas sensor 1 includes a holding member 32 provided within the outer cylinder 26. The collar portion 31b of the insulating contact member 31 is supported by the holding member 32, so that the insulating contact member 31 is held within the outer cylinder 26.

Figure 2:
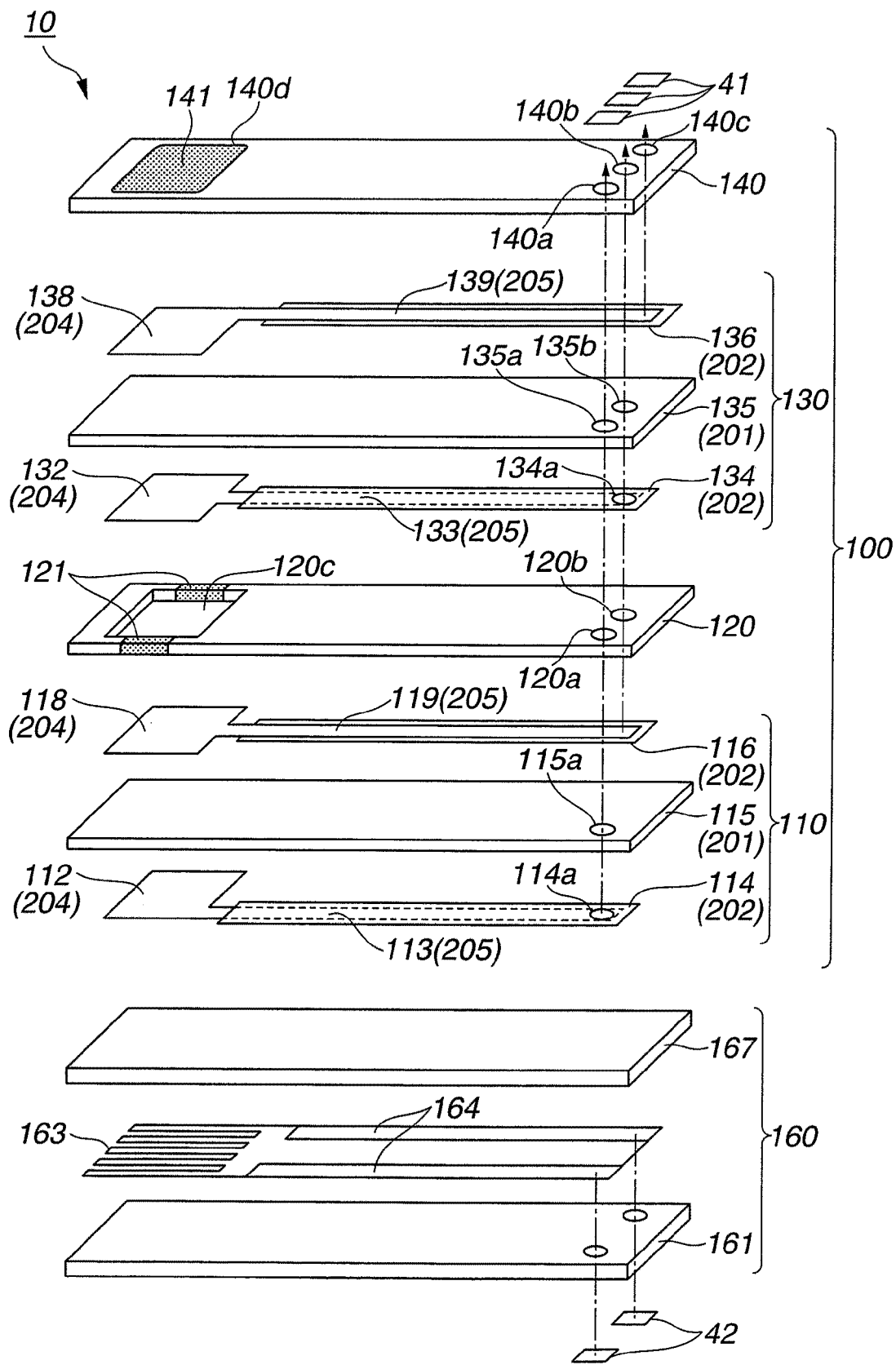
FIG. 2 is an exploded perspective view showing a basic structure of a sensor element used in the gas sensor according to the first embodiment of the present invention.

FIG. 2 is an exploded perspective view showing a sensor element 10 (except for the front end protecting layer 10a) used in the gas sensor 1 according to the embodiments of the present invention. FIG. 2 shows a basic structure in which a sensor lead portion is formed through an insulating layer on a solid electrolyte layer. In FIG. 2, the insulating layer has a flat end portion, as in the conventional gas sensor, and each of the sensor lead portion and the heater lead portion has a single shape which is not divided. However, in the sensor element 10 according to the embodiments of the present invention, these components are arbitrarily varied, as described later.

The sensor element 10 includes an element body 100 having an oxygen concentration sensing cell 110, an interlayer adjusting layer 120, and an oxygen pumping cell 130 which are laminated in this order, and a heater 160 arranged to heat the element body 100.

The oxygen concentration sensing cell 110 includes a first solid electrolyte layer 115 having a first main surface located on a lower side of FIG. 2, and a second main surface located on an upper side of FIG. 2. The oxygen concentration sensing cell 110 includes a first insulating layer 114, a first electrode portion 112, and a first sensor lead portion 113 formed on the first main surface of the first solid electrolyte layer 115; and a second insulating layer 116, a second electrode portion 118, and a second sensor lead portion 119 formed on the second main surface of the first solid electrolyte layer 115.

The first electrode portion 112 has a substantially rectangular shape. The first electrode layer 112 is formed on the first solid electrolyte layer 115 on the front end side (the left side of FIG. 2) of the first insulating layer 114. The first sensor lead portion 113 is connected with a rear end side (the right side of FIG. 2) of the first electrode portion 112. The first sensor lead portion 113 extends in a longitudinal direction of the first solid electrolyte layer 115. The first sensor lead portion 113 has a front end portion (on the left side of FIG. 2) directly formed on the first solid electrolyte layer 115, and a rear end portion (on the right side of FIG. 2) formed through the first insulating layer 114 on the first solid electrolyte layer 115.

The rear end portion (on the right side of FIG. 2) of the first sensor lead portion 113 is electrically connected with one of the electrode terminal portions 41, through a first through hole 114a formed in the first insulating layer 114, a second through hole 115a formed in the first solid electrolyte layer 115, a third through hole 120a formed in the interlayer adjusting layer 120, a sixth through hole 135a formed in a second solid electrolyte layer 135, and an eighth through hole 140a formed in a surface protection layer 140.

The second electrode portion 118 has a substantially rectangular shape. The second electrode portion 118 is formed on the first solid electrolyte layer 115 on the front end side (the left side of FIG. 2) of the second insulating layer 116. The second sensor lead portion 119 extends in the longitudinal direction of the first solid electrolyte layer 115. This second sensor lead portion 119 has a front end portion (on the left side of FIG. 2) directly formed on the first solid electrolyte layer 115, and a rear end portion (on the right side of FIG. 2) formed through the second insulating layer 116 on the first solid electrolyte layer 115.

The rear end portion (on the right side of FIG. 2) of the sensor lead portion 119 is electrically connected with one of the electrode terminal portions 41, through a fourth through hole 120b formed in the interlayer adjusting layer 120, a fifth through hole 134a formed in the third insulating layer 134, a seventh through hole 135b formed in the second solid electrolyte layer 135, and a ninth through hole 140b formed in the surface protection layer 140.

On the other hand, the oxygen pumping cell 130 includes the second solid electrolyte layer 135 having a first main surface located on the lower side of FIG. 2, and a second main surface located on the upper side of FIG. 2. The oxygen pumping cell 130 includes a third insulating layer 134, a third electrode portion 132, and a third sensor lead portion 133 formed on the first main surface of the second solid electrolyte layer 135; and a fourth insulating layer 136, a fourth electrode portion 138, and a fourth sensor lead portion 139 formed on the second main surface of the second solid electrolyte layer 135.

The third electrode portion 132 has a substantially rectangular shape. The third electrode portion 132 is formed on the second electrolyte layer 135 on the front end side (the left side of FIG. 2) of the second insulating layer 134. The third sensor lead portion 133 is connected with a rear end side (on the right side of FIG. 2) of the third electrode portion 132. The third sensor lead portion 133 extends in a longitudinal direction of the second solid electrolyte layer 135. This third sensor lead portion 133 has a front end portion (on the left side of FIG. 2) directly formed on the second solid electrolyte layer 135, and a rear end portion (on the right side of FIG. 2) formed through the fourth insulating layer 136 on the second solid electrolyte layer 135.

The rear end portion (on the right side of FIG. 2) of the third sensor lead portion 133 is electrically connected with one of the electrode portions 41, through the fifth through hole 134a formed in the third insulating layer 134, the seventh through hole 135b formed in the second solid electrolyte layer 135, and the ninth through hole 140b formed in the surface protection layer 140. The sensor lead portion 119 is equal in potential to the third sensor lead portion 133 through the fourth through hole 120b.

The fourth electrode portion 138 has a substantially rectangular shape. The fourth electrode portion 138 is formed on the second solid electrolyte layer 135 on the front end side (the left side of FIG. 2) of the fourth insulating layer 136. The fourth sensor lead portion 139 is connected with a rear end side (on the right side of FIG. 2) of the fourth electrode portion 138. The fourth sensor lead portion 139 extends in the longitudinal direction of the second solid electrolyte layer 135. This fourth sensor lead portion 139 includes a front end portion (on the left side of FIG. 2) directly formed on the second solid electrolyte layer 135, and a rear end portion (on the right side of FIG. 2) formed through the fourth insulating layer 136 on the second solid electrolyte layer 135. The rear end portion (on the right side of FIG. 2) is electrically connected with one of the terminal portions 41 through a tenth through hole 140c formed in the surface protection layer 140.

The interlayer adjusting layer 120 disposed between the oxygen concentration sensing cell 110 and the oxygen pumping cell 130 includes a sensing chamber 120c which is an empty space, and which is sandwiched between the second electrode portion 118 and the third electrode portion 132. The interlayer adjusting layer 120 includes diffusion controlling portions 121 disposed on both sides of the sensing chamber 120c in a widthwise direction, and arranged to control the measurement gas to a constant velocity irrespective of a flow velocity outside the element, and to guide the measurement gas. The diffusion controlling portions 121 are porous so as to guide the measurement gas.

The surface protection layer 140 is laminated on the second solid electrolyte layer 135 to sandwich the fourth electrode portion 138 and the fourth sensor lead portion 139. The surface protection layer 140 includes a through hole 140d located in a position to overlap with the fourth electrode portion 138. An electrode protection portion 141 is fit (mounted) in the through hole 140d of the surface protection layer 140.

On the other hand, the heater includes a first base layer 161 and a second base layer 167 mainly made of alumina; a heating portion 163 mainly made of platinum, and sandwiched between the first base layer 161 and the second base layer 167; and a pair of heater lead portions 164 each extending from the heating portion 163 in a longitudinal direction of the first base layer 161 and so on. The rear ends (on the right side of FIG. 2) of the heater lead portions 164 are connected, respectively, with the heater terminal portions 42 through through holes formed in the first base layer 161.

Hereinafter, the first solid electrolyte layer 115 and the second solid electrolyte layer 135 are referred to as a solid electrolyte layer 201. The first insulating layer 114, the second insulating layer 116, the third insulating layer 134, and the fourth insulating layer 136 are referred to as an insulating layer 202. The first electrode portion 112, the second electrode portion 118, the third electrode portion 132, and the fourth electrode portion 138 are referred to as an electrode portion 204. The first sensor lead portion 113, the second sensor lead portion 119, the third sensor lead portion 133, and the fourth sensor lead portion 139 are referred to as a lead portion 205.

Figure 3A:
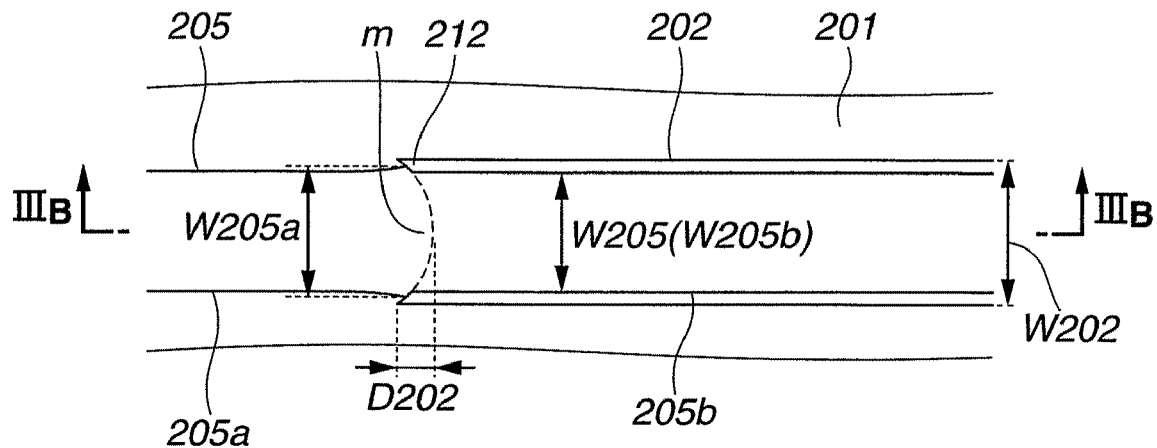
FIG. 3A is a plan view showing an example in which an end portion of an insulating layer has a recessed shape, in the gas sensor according to the first embodiment of the present invention.
Figure 3B:
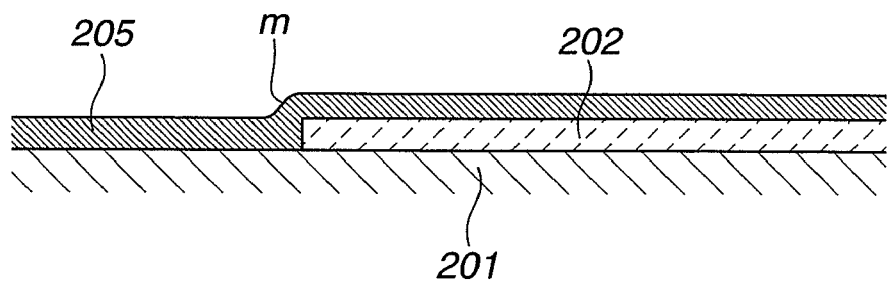
FIG. 3B is a sectional view taken along a section line IIIB-IIIB.

FIG. 3A is a plan view showing an insulating layer 202 of a gas sensor 1 according to a first embodiment of the present invention. FIG. 3B is a sectional view taken along a section line IIIB-IIIB of FIG. 3A. In FIGS. 3-9, a left side of each drawing is a front end side, and a right side of each drawing is a rear end side. In this embodiment, an end portion 212 of the insulating layer 202 has a recessed shape or concave shape which is recessed or concave in the longitudinal direction as viewed in the lamination direction. As shown in FIGS. 3A and 3B, the insulating layer 202 is formed on the solid electrolyte layer 201. The insulating layer 202 includes the end portion 212 on the front end side which has a recessed shape. The lead portion 205 includes a front end portion 205a directly formed on the solid electrolyte layer 201, and a rear end portion 205b formed through the insulating layer 202 on the solid electrolyte layer 201. That is, the insulating layer 202 is sandwiched between the rear end portion 205b of the lead portion 205 and the solid electrolyte layer 201, as shown in FIG. 3B.

By thus-formed insulating layer 202 with the recessed end portion 212, the conductive paste can be printed to gently ascend a corner portion of the end portion 212 of the insulating pattern 202 from the both sides of the end portion 212 of the insulating pattern 202 in the widthwise directions (upward and downward directions in FIG. 3A) when the conductive paste is printed from the front end side to the rear end side at the time of manufacture. On the other hand, the conductive paste can be printed to descend the corner portion of the end portion 212 of the insulating patter 202 from a center portion of the end portion 212 of the insulating pattern 202 in the widthwise direction when the conductive paste is printed in the opposite direction (from the rear end side to the front end side). Accordingly, in either cases, it is possible to increase a thickness of an astride portion m of the lead pattern 205 which extends over and across (astride) the end portion 212 of the insulating pattern 202, relative to the thickness in the conventional gas sensor. Moreover, the lead portion 205 can gently extend over and across the end portion 212 of the insulating pattern 202. Therefore, it is possible to suppress the generation of crack in the lead pattern 205 which extends over and across the end portion 212 of the insulating pattern 202, even when the lead pattern 205 is contracted during the drying and the baking.

Figure 4:
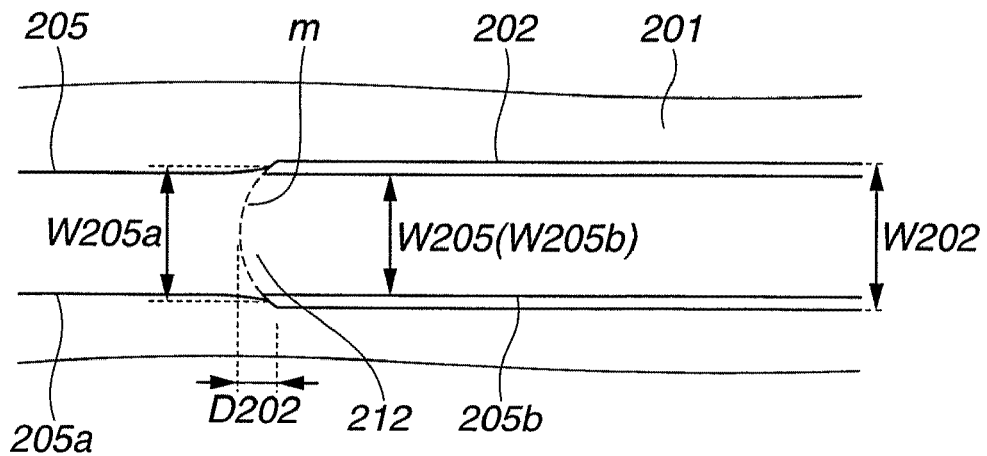
FIG. 4 is a plan view showing an example in which an end portion of an insulating layer has a raised shape, in a gas sensor according to a second embodiment of the present invention.

FIG. 4 is a plan view showing an insulating layer 202 of a gas sensor 1 according to a second embodiment of the present invention. In this embodiment, the end portion 212 of the insulating layer has a raised shape or convex shape which is raised or convex in the longitudinal direction, as viewed in the lamination direction. By thus-formed insulating layer 202 with the raised end portion 212, the conductive paste can be printed to gently ascend the corner portion of the end portion 212 of the insulating pattern 202 from the center portion of the end portion 212 of the insulating layer 202 in the widthwise direction when the conductive paste is printed from the front end side to the rear end side at the time of manufacture. On the other hand, the conductive paste can be printed to gently descend the corner portion of the end portion 212 of the insulating pattern 202 from the both sides of the end portion 212 of the insulating pattern 202 in the widthwise direction when the conductive paste is printed in the opposite direction (from the rear end side to the front end side). Accordingly, in either cases, it is possible to increase the thickness of the astride portion m of the lead pattern 205 which extends over and across (astride) the end portion 212 of the insulating pattern 202, relative to the thickness in the conventional gas sensor. Moreover, the lead pattern 205 can gently extend over and across the end portion 212 of the insulating pattern 202. Therefore, it is possible to suppress the generation of the crack in the lead pattern 205 which extends over and across the end portion 212 of the insulating pattern 202 even when the lead pattern 205 is contracted during the drying and the baking.

Figure 5:
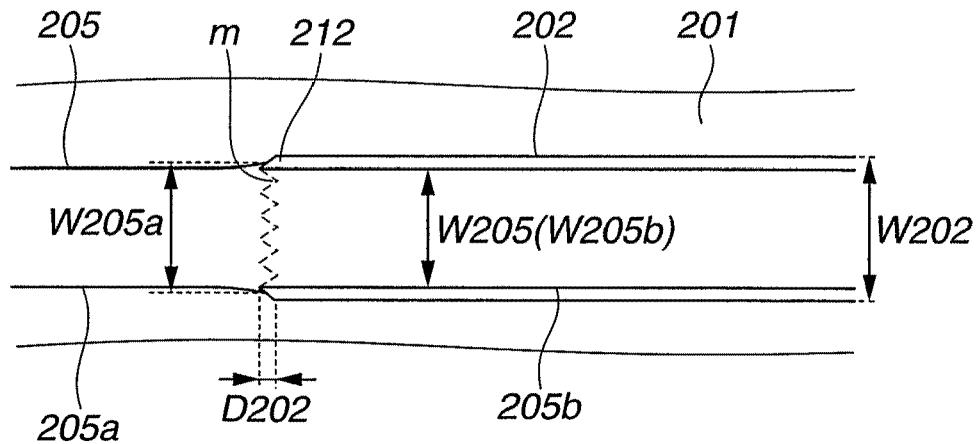
FIG. 5 is a plan view showing an example in which an end portion of an insulating layer has a recessed and raised shape, in a gas sensor according to a third embodiment of the present invention.

FIG. 5 is a plan view showing an insulating layer 202 of a gas sensor 1 according to a third embodiment of the present invention. In this embodiment, the end portion 212 of the insulating layer 202 has a recessed and raised shape or concave-convex shape which has a plurality of raised portions raised in the longitudinal direction, and a plurality of recessed portions recessed in the longitudinal direction. By thus-formed insulating layer 202 with the recessed and raised end portion 212, the conductive paste can be printed to gently ascend the corner portion of the end portion 212 of the insulating pattern 202 from a center portion of each raised portion of the end portion 212 of the insulating layer 202 in the widthwise direction when the conductive paste is printed from the front end side to the rear end side at the time of manufacture. On the other hand, the conductive paste can be printed to gently descend the corner portion of the end portion 212 of the insulating pattern 202 from the both sides of each recessed portion of the end portion 212 of the insulating pattern 202 in the widthwise direction when the conductive paste is printed from the opposite direction (from the rear end side to the front end side). Accordingly, it is possible to increase a thickness of an astride portion m of the lead pattern 205 which extends over and across (astride) the end portion 212 of the insulating pattern 202, relative to the thickness in the conventional gas sensor. Moreover, the lead pattern 205 can gently extend over and across the end portion 212 of the insulating pattern 205. Therefore, it is possible to suppress the generation of the crack in the lead pattern 205 which extends over and across the end portion 212 of the insulating pattern 202 even when the lead pattern 205 is contracted during the drying and the baking.

In this way, in the first gas sensors 1 according to the first to third embodiments, the end portion 212 of the insulating layer 202 over and across which the lead portion 205 of the sensor element 10 extends have the recessed shape, the raised shape, and the recessed and raised shape. Accordingly, the thickness of the lead portion 205 which extends over and across the end portion 212 of the insulating layer 202 is increased. The lead portion 205 gently extends over and across the end portion 212 of the insulating layer 202. Therefore, it is possible to suppress the generation of the crack in the lead portion 205 at the time of manufacture, and to accurately sense the concentration.

It is preferable that the end portion 212 of the insulating layer 202 has the recessed shape in case of comparing the recessed shape with the raised shape, although the shape of the end portion 212 of the insulating layer 202 is not limited to the recessed shape. By the end portion 212 of the insulating layer 202 with the recessed shape, it is possible to suppress the conductive paste from protruding from the both sides of the end portion 212 of the insulating pattern 202 in the widthwise direction when the conductive paste is printed for forming the lead pattern 205 at the time of manufacture.

That is, the conductive paste is printed to collect the conductive paste from the both sides of the end portion 212 of the insulating pattern 202 in the widthwise direction to the center portion when the conductive paste is printed from the front end side to the rear end side in a case in which the end portion 212 of the insulating layer 202 has the recessed shape as shown in FIG. 3. Accordingly, it is possible to suppress the conductive paste from protruding from the both sides in the widthwise direction. On the other hand, the conductive paste is held by the both side portions of the end portion 212 of the insulating pattern 202 in the widthwise direction when the conductive paste is printed from the opposite direction. Therefore, it is possible to prevent the deterioration of the appearance. Moreover, it is possible to suppress unnecessary catalytic reaction (catalysis) and so on, and to accurately sense the concentration.

As shown in FIGS. 3A, 4 and 5, a width W202 of the insulating layer 202 is larger than a width W205 of the lead portion 205. Accordingly, it is possible to suppress the lead pattern 205 from protruding from the both sides of the insulating pattern 202 in the widthwise direction. Therefore, it is possible to prevent the deterioration of the appearance. Moreover, it is possible to suppress the unnecessary catalytic reaction (catalysis) and so on, and to accurately sense the concentration. Furthermore, it is preferable that the width W202 of the insulating layer 202 is 1.1 times larger than the width W205 of the lead portion 205.

As shown in FIGS. 3A, 4 and 5, the end portion 205a of the lead portion 205 includes a large width portion which is located near the end portion 212 of the insulating layer 202, and which has a width increasing toward the rear end side. That is, near the end portion 212 of the insulating layer 202, the width W205a of the front end portion 205a of the lead portion 205 is larger than the width W205b of the rear end portion 205b of the lead portion 205. In this way, the lead portion 205 has the large width portion which has the width increasing toward the rear end side. Accordingly, the lead portion 205 can readily gently extend over and across the end portion 212 of the insulating layer 202. Moreover, it is possible to further suppress the generation of the crack in the lead portion 205, and to accurately sense the concentration.

Moreover, it is preferable that a ratio (D202/W202) of a depth (length) D202 to the width W202 of the end portion 212 of the insulating layer 202 is equal to or larger than 0.1 in a case in which the end portion 212 of the insulating layer 202 has the recessed shape as shown in FIG. 3. Furthermore, it is preferable that a ratio (D202/W202) of a height (length) D202 to the width W202 of the end portion 212 of the insulating layer 202 is equal to or larger than 0.1 in a case in which the end portion 212 of the insulating layer 202 has the raised shape as shown in FIG. 4. Moreover, it is preferable that a ratio (D202/W202) of a height (length) D202 of each raised portion to the width W202 of the end portion 212 is equal to or larger than 0.1 in a case in which the end portion 212 of the insulating layer 202 has the recessed and raised shape as shown in FIG. 5. With these, it is possible to effectively print the conductive paste on the end portion 212 of the insulating pattern 202 when the conductive paste is printed for forming the lead pattern 205 at the time of manufacture, and to sufficiently increase the thickness.

Figure 6A:
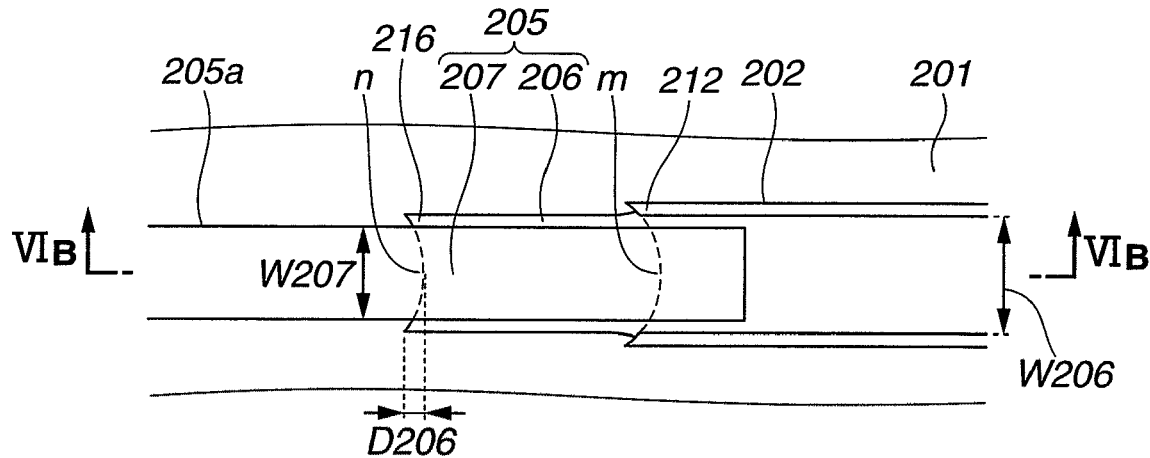
FIG. 6A is a plan view showing an example in which an end portion of a first lead portion has a recessed shape, in a gas sensor according to a fourth embodiment of the present invention.
Figure 6B:
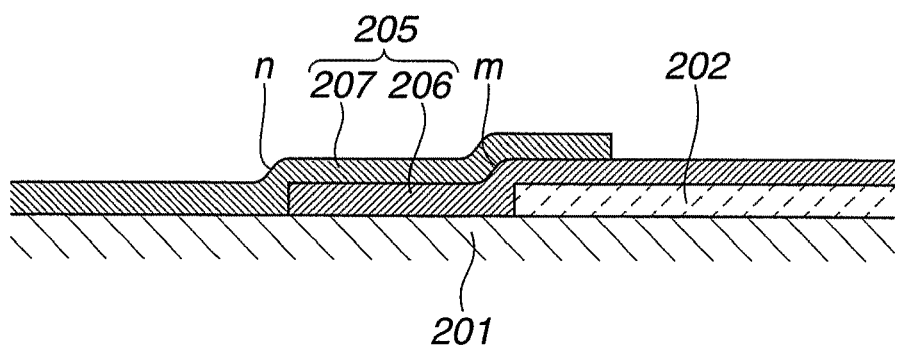
FIG. 6B is a sectional view taken along a section line VIB-VIB of FIG. 6A.

FIG. 6A is a plan view showing an insulating layer 202 and a lead portion 205 of a gas sensor 1 according to a fourth embodiment of the present invention. FIG. 6B is a sectional view VIB-VIB of FIG. 6A. In this fourth embodiment, the lead portion 205 includes a first lead portion 206 and a second lead portion 207. The first lead portion 206 includes an end portion 216 having a recessed shape or concave shape which is recessed (concave) in the longitudinal direction as viewed in the lamination direction. The first lead portion 206 includes a front end portion formed on the solid electrolyte layer 201, and a rear end portion formed through the insulating layer 202 on the solid electrolyte layer 201. The first lead portion 206 includes the end portion 216 on the front end side, and which has a recessed shape recessed in the longitudinal direction. The second lead portion 207 includes a front end portion directly formed on the solid electrolyte layer 201, and a rear end portion formed through the insulating layer 202 and the first lead portion 206 on the solid electrolyte layer 201.

By thus-formed first lead portion 206 with the recessed end portion 216, the conductive paste can be printed to gently ascend the corner portion of the end portion 216 of the first lead pattern 206 from the both sides of the end portion 216 of the first lead pattern 206 in the widthwise direction when the conductive paste is printed from the front end side to the rear end side for forming the second lead pattern 207 at the time of manufacture. On the other hand, the conductive paste can be printed to gently descend the corner portion of the end portion 216 of the first lead pattern 206 from the center portion of the end portion 216 of the first lead pattern 206 in the widthwise direction when the conductive paste is printed from the opposite direction (from the rear end side to the front end side). Accordingly, in either cases, it is possible to increase the thickness of an astride portion n of the second lead pattern 207 which extends over and across (astride) the end portion 216 of the first lead pattern 206, relative to the thickness in the conventional gas sensor. Moreover, it is possible to gently extend over and across the end portion 216 of the first lead pattern 206. Therefore, it is possible to suppress the generation of the crack in the second lead pattern 207 which extends over and across the end portion 216 of the first lead pattern 206 even when the second lead pattern 207 is contracted during the drying and the baking.

Figure 7:
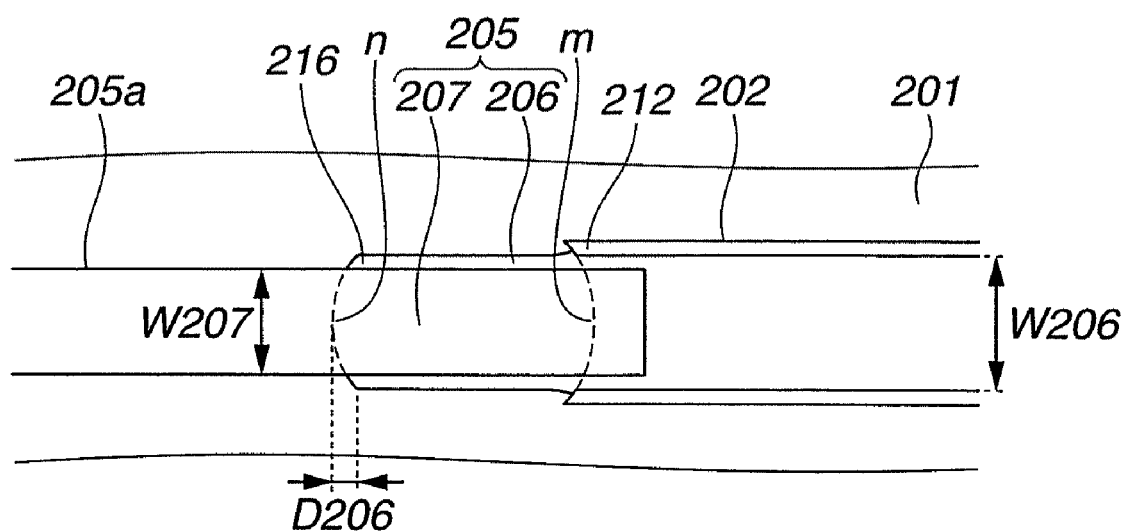
FIG. 7 is a plan view showing an example in which an end portion of a first lead portion has a raised shape, in a gas sensor according to a fifth embodiment of the present invention.

FIG. 7 is a plan view showing an insulating layer 202 and a lead portion 205 of a gas sensor 1 according to a fifth embodiment of the present invention. In the fifth embodiment, the end portion 216 of the first lead portion 206 has a raised shape or convex shape which is raised or convex in the longitudinal direction as viewed in the lamination direction.

By thus-formed first lead portion 206 with the raised end portion 216, the conductive paste can be printed to gently ascend the corner portion of the end portion 216 of the first lead pattern 206 from the center portion of the end portion 216 of the first lead pattern 206 in the widthwise direction when the conductive paste is printed from the front end side to the rear end side for forming the second lead pattern 207 at the time of manufacture. On the other hand, the conductive paste can be printed to gently descend the end portion 216 of the first lead pattern 206 from the both sides of the end portion 216 of the first lead pattern 206 in the widthwise direction when the conductive paste is printed from the opposite direction (from the rear end side to the front end side). Accordingly, in either cases, it is possible to increase the thickness of the astride portion n of the second lead pattern 207 which extends over and across (astride) the end portion 216 of the first lead pattern 206, relative to the thickness in the conventional gas sensor. Moreover, it is possible to gently extend over and across the end portion 216 of the first lead pattern 206. Therefore, it is possible to suppress the generation of the crack in the second lead pattern 207 which extends over and across the end portion 216 of the first lead pattern 206 even when the second lead pattern 207 is contracted during the drying and the baking.

Figure 8:
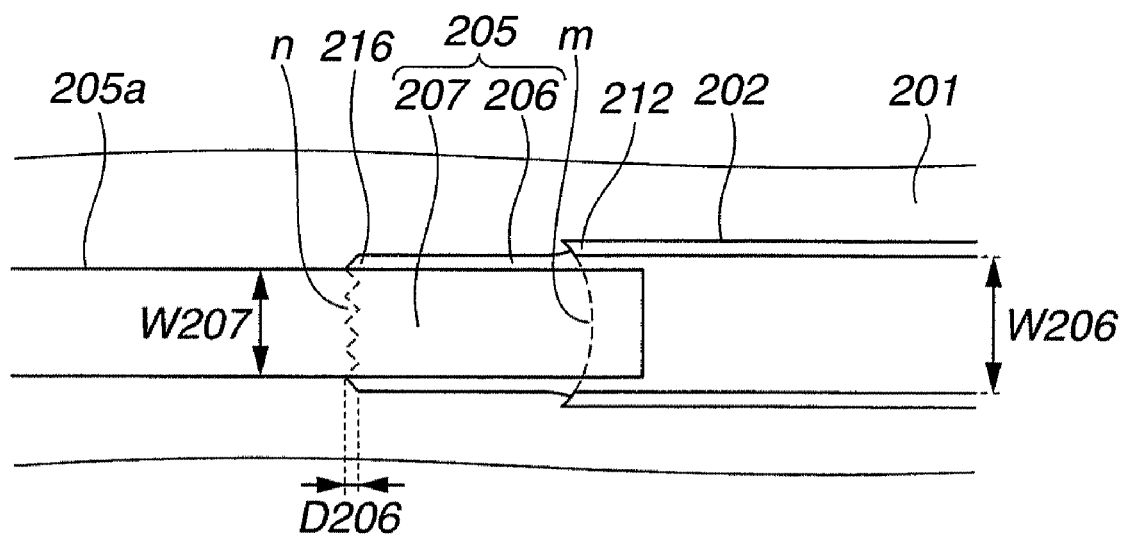
FIG. 8 is a plan view showing an example in which an end portion of a first lead portion has a recessed and raised shape, in a gas sensor according to a sixth embodiment of the present invention.
Figure 9A:
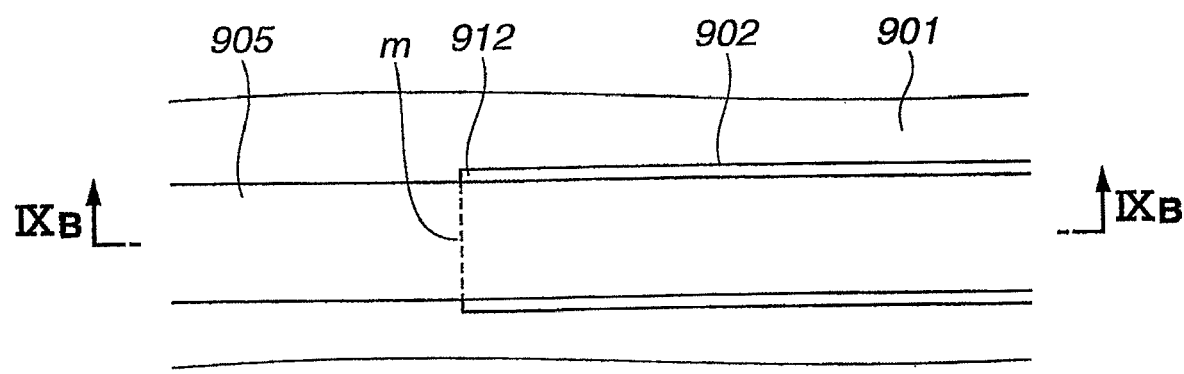
FIG. 9A is a plan view showing an example of a conventional sensor element.
Figure 9B:
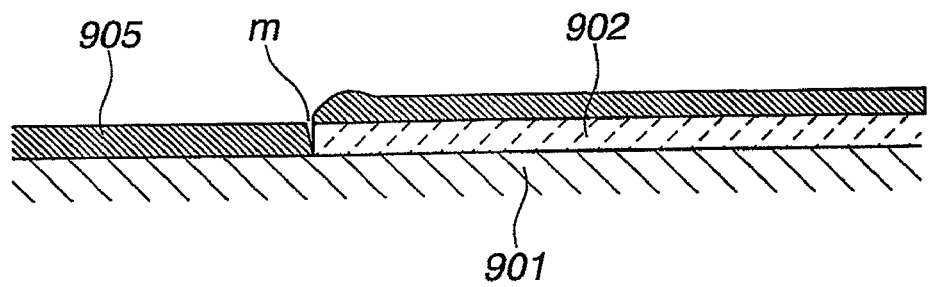
FIG. 9B is a sectional view taken along a section line IXB-IXB.

FIG. 8 is a plan view showing an insulating layer 202 and a lead portion 205 of a gas sensor 1 according to a sixth embodiment of the present invention. In the sixth embodiment, the end portion 216 of the first lead portion 206 has a recessed and raised shape (concave-convex shape) which has a plurality of raised portions raised in the longitudinal direction, and a plurality of recessed portions recessed in the longitudinal direction. By the first lead portion 206 with the recessed and raised end portion 216, the conductive paste can be printed to gently ascend the corner portion of the end portion 216 of the first lead pattern 206 from the center portion of each raised portion of the end portion 216 of the first lead pattern 206 in the widthwise direction when the conductive paste is printed from the front end side to the rear end side for forming the second led pattern 207 at the time of manufacture. On the other hand, the conductive paste can be printed to gently descend the corner portion of the end portion 216 of the first lead pattern 206 from the both sides of each recessed portion of the end portion 216 of the first lead pattern 206 in the widthwise direction when the conductive paste is printed from the opposite direction (from the rear end side to the front end side). Accordingly, in either cases, it is possible to increase the thickness of the astride portion n of the second lead pattern 207 which extends over and across (astride) the end portion 216 of the first lead pattern 206, relative to the thickness in the conventional gas sensor. Moreover, it is possible to gently extend over and across the end portion 216 of the first lead pattern 206. Therefore, it is possible to suppress the generation of the crack in the second lead pattern 207 which extends over and across the end portion 216 of the first lead pattern 206 even when the second lead pattern 207 is contracted during the drying and the baking.

In the fourth to sixth embodiments, the lead portion 205 includes the first lead portion 206 and the second lead portion 207. Accordingly, it is possible to attain the high performance by dividing the function. In a case in which, for example, the second lead portion 207 connected with the electrode portion 204 is mainly made of noble metal as in the conventional gas sensor, it is possible to form the second lead portion 207 by printing the conductive paste concurrently with the electrode portion 204 which needs the catalysis. Moreover, it is possible to decrease the use of the noble metal in the first lead portion 206 connected with the electrode terminal portion 41. Moreover, the second lead portion 207 extends over and across the end portion 216 of the first lead portion 206. Accordingly, it is possible to ensure the electrical connection between the first lead portion 206 and the second lead portion 207.

Moreover, the end portion 216 of the first lead portion 206 over and across which the second lead portion 207 extends has the recessed shape, the raised shape, and the recessed and raised shape. Accordingly, it is possible to suppress the generation of the crack in the astride portion of the second lead portion 207 which extends over and across the end portion 216 of the first lead portion 206. Moreover, it is possible to accurately sense the concentration.

Moreover, it is preferable that the end portion of the first lead portion 206 has the recessed shape in case of comparing the recessed shape with the raised shape, although the shape of the end portion is not limited to the recessed shape. By the end portion 216 of the first lead portion 206 with the recessed shape, it is possible to suppress the conductive paste from protruding from the both sides of the end portion 216 of the first lead pattern 206 in the widthwise direction when the conductive paste is printed for forming the second lead pattern 207 at the time of manufacture of the sensor element 10.

That is, the conductive paste is printed to collect the conductive paste from the both sides of the end portion 216 of the first lead pattern 206 in the widthwise direction toward the center potion when the conductive paste is printed from the front end side to the rear end side in a case in which the end portion 216 of the first lead portion 206 has the recessed shape as shown in FIG. 6. Accordingly, it is possible to suppress the conductive paste from protruding in the widthwise direction. On the other hand, the conductive paste is held by the both side portions of the end portion 216 of the insulating pattern 206 in the widthwise direction. Therefore, it is possible to prevent the deterioration of the appearance, to suppress unnecessary catalytic reaction (catalysis) and so on, and to accurately sense the concentration.

Moreover, it is preferable that a ratio (D206/W206) of the length (depth) D206 to the width W206 of the end portion 216 of the first lead portion 206 is equal to or larger than 0.1 in a case in which the end portion 216 of the first lead portion 206 has the recessed shape as shown in FIG. 6. Furthermore, it is preferable that a ratio (D206/W206) of a length (height) D206 to the width W206 of the end portion 216 of the first lead portion 206 is equal to or larger than 0.1 in a case in which the end portion 216 of the first lead portion 206 has the raised shape as shown in FIG. 7. Moreover, it is preferable that a ratio of the length (height) D of each raised portion to the width W206 of the end portion 216 of the first lead portion 206 is equal to or larger than 0.1 in a case in which the end portion 216 of the first lead portion 206 has the recessed and raised shape as shown in FIG. 8. By thus-formed gas sensor, it is possible to effectively print the conductive paste on the end portion 216 of the first lead pattern 206 when the conductive paste is printed for forming the second lead pattern 207 at the time of manufacture, and to sufficiently increase the thickness.

Moreover, it is preferable that the width W206 of the first lead portion 206 disposed on the solid electrolyte layer 201 side is larger than the width W207 of the second lead portion 207, as shown in FIGS. 6A, 7 and 8. Furthermore, it is preferable that, for example, the width W206 of the first lead portion 206 is 1.1 times larger than the width W207 of the second lead portion 207. In this way, the width W206 of the first lead portion 206 generally formed prior to the second lead portion 207 is larger than the width W207 of the second lead portion 207 formed after the first lead portion 206. Accordingly, it is possible to suppress the conductive paste from protruding from the both sides of the first lead pattern 206 in the widthwise direction when the conductive paste is printed for forming the second lead pattern 207 at the time of manufacture.

The end portion 216 of the first lead portion 206 is located in a position different from the position of the end portion 212 of the insulating layer 202, as shown in FIGS. 6A, 7 and 8. In a case in which the end portion 216 of the first lead portion 206 is located just above the end portion 212 of the insulating layer 202, this overlapped portion has a complicated shape. Accordingly, the sensor element 10 tends to break. Moreover, the second lead portion 207 needs to extend over and across the end portion 212 of the insulating layer 202 and the end portion 216 of the first lead portion 206 at one time. Therefore, the portion of the second lead portion 207 which extends over and across the end portion of the insulating layer and the end portion of the first lead portion becomes high, and the crack may generate at the time of manufacture. On the other hand, in the above-mentioned embodiments, the sensor element 10 has a simple shape, and the sensor element 10 does not break. Moreover, it is not necessary that the second lead portion 207 extends over and across the end portion 212 of the insulating layer 202 and the end portion 216 of the first lead portion 206 at one time. Therefore, it is possible to suppress the generation of the crack in the lead portion 205.

It is preferable that the end portion 216 of the first lead portion 206 is formed at the front end portion 205a of the lead portion 205, as shown in FIGS. 6A, 7 and 8. With this, the sensor element 10 does not have the extra thickness, and the surface protection layer 140 is laminated on the solid electrolyte layer 201 without the clearance.

Moreover, it is preferable that the second lead portion 207 extends over and across the end portion 212 of the insulating layer 202, as shown in FIGS. 6A, 7 and 8. With this, it is possible to improve the reliability of the electrical connection between the first lead portion 206 and the second lead portion 207.

The present invention is not limited to the above-mentioned embodiments. It is possible to vary the gas sensors according to the embodiments. In the embodiments, the gas sensor element is the oxygen sensor element. However, the sensor element is not limited to the oxygen sensor element. For example, the sensor element may be an NOx sensor element arranged to sense concentration of NOx.

In the gas sensor according to the embodiments of the present invention, a gas sensor includes a substantially cylindrical metal shell 2; a laminated sensor element 10 held within the metal shell 2, the sensor element 10 including: a plate-shaped solid electrolyte layer 201 extending in a longitudinal direction; an electrode portion 204 provided on the solid electrolyte layer 201; an insulating layer 202; and a lead portion 205 connected with the electrode portion 204, the lead portion 205 extending in the longitudinal direction, and having a front end portion 205a laminated on the solid electrolyte layer 201, and a rear end portion 205b laminated through the insulating layer 202 on the solid electrolyte layer 201, the insulating layer 202 having an end portion 212 over and across which the lead portion 205 extends, and which has a recessed shape, a raised shape, or a recessed and raised shape in the longitudinal direction as viewed in the lamination direction.

In the gas sensor according to the embodiments of the present invention, the end portion of the insulating layer over and across which the lead portion extends has the recessed shape, the raised shape, or the recessed and raised shape in the longitudinal direction, as viewed in the lamination direction. Accordingly, the thickness of the lead portion which extends over and across the end portion of the insulating layer increases. Moreover, the lead portion gently extends over and across the end portion of the insulating layer. Therefore, it is possible to suppress the generation of the crack in the lead portion at the time of manufacture, and to accurately sense the concentration.

In the gas sensor according to the embodiments of the present invention, the insulating layer 202 has a width W202 in a direction perpendicular to the longitudinal direction which is larger than a width W205 of the lead portion 205 in the direction perpendicular to the longitudinal direction. Accordingly, it is possible to suppress the lead portion from protruding from the both sides of the insulating layer in the widthwise direction. Therefore, it is possible to prevent the deterioration of the appearance. Moreover, it is possible to suppress the unnecessary catalytic reaction (catalysis) and so on, and to accurately sense the concentration.

In the gas sensor according to the embodiments of the present invention, the front end portion 205*a* of the lead portion 205 located near the end portion 212 of the insulating layer 202 has a width W205*a* larger than a width W205*b* of the rear end portion 205*b* of the lead portion 205. The lead portion has the wide front end portion (tapered front end portion). Accordingly, it is possible to gently extend over and across the end portion of the insulating layer. Moreover, it is possible to further suppress the generation of the crack in the lead portion, and to accurately sense the concentration.

In the gas sensor according to the embodiments of the present invention, the end portion 212 of the insulating layer 202 satisfies a relationship of D/W≧0.1, where W represents a width W202 of the insulating layer 202, and D represents a length between a front end and a rear end of the end portion 212 of the insulating layer 202 in the longitudinal direction. Accordingly, it is possible to sufficiently increase the thickness of the lead portion which extends over and across the end portion of the insulating layer. Moreover, it is possible to further suppress the generation of the crack in the lead portion, and to accurately sense the concentration.

In the gas sensor according to the embodiments of the present invention, the lead portion 205 includes a first lead portion 206 having an end portion 216 having a recessed shape, a raised shape, or a recessed and raised shape in the longitudinal direction as viewed in the lamination direction, and a second lead portion 207 extending over and across the end portion 216 of the first lead portion 206.

It is considered that the lead portion is divided into a front end side portion (second lead portion) connected with the electrode portion and a rear end side portion (first lead portion) for the reduction of the noble metal such as the platinum. Specifically, the rear end side portion of the lead portion does not need catalysis, and the rear end side portion of the lead portion is provided for electrically connecting the electrode portion with the outside. Accordingly, it is possible to decrease the use of the noble metal in the rear end side portion of the lead portion. On the other hand, the front end side portion of the lead portion is provided as a terminal portion of the electrode portion. The front side end portion of the lead portion is formed by printing the conductive paste concurrently with the forming of the electrode portion.

In a case in which the sensor lead portion is divided in this way, it is necessary to superimpose an end portion of front end side portion which is a connection portion, on an end portion of the rear end side portion for ensuring the electrical connection. In this case, the end portion of the first lead portion has the recessed shape, the raised shape, and the recessed and raised shape in the longitudinal direction. Accordingly, the thickness of the second lead portion which extends over and across the end portion of the first end portion increases. The second lead portion gently extends over and across the end portion of the first lead portion. Therefore, it is possible to suppress the generation of the crack in the lead portion at the time of manufacture, and to accurately sense the concentration.

In the gas sensor according to the embodiments of the present invention, the end portion 212 of the insulating layer 202 is located in a position different from a position of the end portion 216 of the first lead portion 206 in the longitudinal direction of the sensor element 10. In a case in which the end portion of the first lead portion is overlapped on the end portion of the insulating layer, the overlapped portion has a complicated shape. The sensor element may break. Moreover, it is necessary that the second lead portion extends over and across the end portion of the insulating layer and the end portion of the first lead portion at one time. Accordingly, the portion of the second lead portion which extends over and across the end portion of the insulating layer and the end portion of the first lead portion becomes high, and the crack may generate at the time of manufacture. On the other hand, in the gas sensor according to the embodiment of the present invention, the sensor element has the simple shape, and the sensor element does not break. Moreover, it is unnecessary that the second lead portion extends over and across the end portion of the insulating layer and the end portion of the first lead portion at one time. Accordingly, it is possible to suppress the generation of the crack in the lead portion.

In the gas sensor according to the embodiments of the present invention, the end portion 216 of the first lead portion 206 is formed in the front end portion 205*a* of the lead portion 205. Accordingly, it is possible to laminate other layers on the solid electrolyte layer to cover the lead portion and the insulating layer, without clearance between the solid electrolyte layer and the other layers.

In the gas sensor according to the embodiments of the present invention, the second lead portion 207 extends over and across the end portion 212 of the insulating layer 202. The end portion of the insulating layer is disposed near the electrode portion for separating the lead portion from the solid electrolyte layer. Consequently, the end portion of the first lead portion is located near the end portion of the insulating layer. In this case, the second lead portion extends over and across the end portion of the insulating layer. Therefore, it is possible to improve the electrical connection between the first lead portion and the second lead portion.

In the gas sensor according to the embodiments of the present invention, the gas sensor element 10 is an NOx sensor element arranged to sense an NOx concentration.

The entire contents of Japanese Patent Application No. 2008-178999 filed Jul. 9, 2008 and Japanese Patent Application No. 2009-130245 filed May 29, 2009 are incorporated herein by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. A gas sensor comprising:
   a substantially cylindrical metal shell;
   a laminated sensor element held within the metal shell, the sensor element including:
   a plate-shaped solid electrolyte layer extending in a longitudinal direction;

an electrode portion laminated on the solid electrolyte layer; and a lead portion connected with the electrode portion and extending in the longitudinal direction, wherein the sensor element includes an insulating layer laminated on the solid electrolyte layer; and the lead portion has a front end portion laminated on the solid electrolyte layer, and a rear end portion laminated through the insulating layer on the solid electrolyte layer, wherein the insulating layer has an end portion over and across which the lead portion extends, and the end portion of the insulation layer has a recessed shape or a raised shape in the longitudinal direction as viewed in the lamination direction, and wherein the recessed shape of the end portion of the insulation layer is an entirely concave shape or the raised shape of the end portion of insulation layer is an entirely convex shape.

2. The gas sensor as claimed in claim 1, wherein the gas sensor element is an NOx sensor element arranged to sense an NOx concentration.

3. The gas sensor as claimed in claim 1, wherein the solid electrolyte layer has a surface on which the front end portion of the lead portion is laminated; the insulating layer has a surface on which the rear end portion of the lead portion is laminated; and the surface of the solid electrolyte layer and the surface of the insulating layer form a stepped shape.

4. The gas sensor as claimed in claim 1, wherein the insulating layer is laminated entirely on the solid electrolyte layer.

5. The gas sensor as claimed in claim 1, wherein the end portion of the insulating layer satisfies a relationship of $D/W \geq 0.1$, where W represents a width of the insulating layer, and D represents a length between a front end and a rear end of the end portion of the insulating layer in the longitudinal direction.

6. The gas sensor as claimed in claim 1, wherein the insulating layer has a width in a direction perpendicular to the longitudinal direction which is larger than a width of the lead portion in the direction perpendicular to the longitudinal direction.

7. The gas sensor as claimed in claim 6, wherein the front end portion of the lead portion located near the end portion of the insulating layer has a width larger than a width of the rear end portion of the lead portion.

8. The gas sensor as claimed in claim 6, wherein the width of the insulating layer is smaller than a width of the solid electrolyte layer.

9. The gas sensor as claimed in claim 1, wherein the lead portion includes a first lead portion having an end portion having a recessed shape, a raised shape, or a recessed and raised shape in the longitudinal direction as viewed in the lamination direction, and a second lead portion extending over and across the end portion of the first lead portion.

10. The gas sensor as claimed in claim 9, wherein the end portion of the insulating layer is located in a position different from a position of the end portion of the first lead portion in the longitudinal direction of the sensor element.

11. The gas sensor as claimed in claim 10, wherein the end portion of the first lead portion is formed in the front end portion of the lead portion.

12. The gas sensor as claimed in claim 11, wherein the second lead portion extends over and across the end portion of the insulating layer.

* * * * *